United States Patent [19]

Suzuki et al.

[11] Patent Number: 4,933,122

[45] Date of Patent: Jun. 12, 1990

[54] PROCESS AND APPARATUS FOR PRODUCING BEADS

[75] Inventors: Akira Suzuki, Tokyo; Yuji Sakamoto, Kitsuregawa, both of Japan

[73] Assignee: Kirin Beer Kabushiki Kaisha, Tokyo, Japan

[21] Appl. No.: 155,248

[22] Filed: Feb. 12, 1988

[30] Foreign Application Priority Data

Feb. 13, 1987 [JP] Japan .................. 62-31223

[51] Int. Cl.⁵ ............................................. B29B 9/10
[52] U.S. Cl. .......................................... 264/13; 264/4;
264/7; 425/5; 425/10; 427/2; 427/4; 435/174
[58] Field of Search .................. 264/4, 7, 13, 14;
425/5, 6, 10; 427/2, 4, 212; 435/174

[56] References Cited

U.S. PATENT DOCUMENTS

| | | | |
|---|---|---|---|
| 1,614,636 | 1/1927 | Wachtel | 425/10 |
| 2,446,783 | 8/1948 | Payne | 425/10 |
| 4,352,883 | 10/1982 | Lim | 264/4 |
| 4,391,909 | 7/1983 | Lim | 264/4 |

FOREIGN PATENT DOCUMENTS 0167690 1/1983 European Pat. Off. ............... 264/4

Primary Examiner—Jan H. Silbaugh
Assistant Examiner—Mary Lynn Fertig
Attorney, Agent, or Firm—Limbach, Limbach & Sutton

[57] ABSTRACT

Bead producing process and an apparatus in which sol having enzymes, plant tissues, etc. dispersed therein is dropped into a solidifying liquid through a perforated plate. The sol is fed from a sol supply tank to a position near of the outer periphery of the planet gear of a planetary gear mechanism which is disposed on the perforated plate. At this moment, the sol supply tank is raised at a given rate in proportion to a decrease in the liquid level thereof so that the liquid level of the sol in the sol supply tank may be kept constant with respect to the perforated plate.

8 Claims, 4 Drawing Sheets $r_1\theta = r_2\theta_2$ $\theta_1 + \theta_2 = \theta_1(1 + \frac{r_1}{r_2})$

4,933,122

PROCESS AND APPARATUS FOR PRODUCING BEADS

BACKGROUND OF THE INVENTION

This invention relates to a method and apparatus for producing gel beads immobilizing or enclosing enzymes, plant tissues, etc.

Known methods for producing gel beads by dropping sol include distributing sol in a solidifying liquid tank from the periphery of a rotary disk, and dropping sol from nozzles or orifices formed in a perforated plate. Japanese Patent Laid-Open Publication No. 52521/1984, for example, discloses a method using a perforated plate. In the apparatus used for this method, a perforated plate is provided at the bottom of a sol liquid tank, then sol liquid is added to the tank to a given level, and thereafter pressure is applied to the surface of the sol liquid forcing the sol liquid through the orifices in the perforated plate into the reaction liquid.

In the prior art method, as described above, sol liquid is reserved on the perforated plate up to a given level, and then a pressure is applied to the liquid surface so as to improve productivity. However, since a large quantity of the sol liquid is fed onto the perforated plate, there is a possibility that the resultant beads are inhomogeneous. In addition, in the prior art apparatus the liquid level is feedback controlled, which makes its operation complicated and requires that the apparatus be strong enough to bear the pressure applied to the liquid surface. Furthermore, since the amount of sol is controlled by opening and closing a valve, there is a possibility that plant tissues, may be broken by valve opening and closing operations. The prior art apparatus is therefore not suitable for producing beads, which enclose plant tissues, therein.

SUMMARY OF THE INVENTION

An object of this invention is to provide a bead producing method and apparatus having a simple structure, being capable of producing homogeneous beads, and attaining high productivity.

The present invention provides a bead producing method for dropping sol having enzymes, plant tissues, etc. dispersed therein through a perforated plate into a solidifying liquid, which comprises the steps of: feeding the sol from a sol supply tank to a position near the outer periphery of a planet gear of a planetary gear mechanism disposed on the perforated plate; and moving up the sol supply tank in proportion to a decrease in the liquid level of the sol supply tank whereby the liquid level may be retained in a constant position with respect to the perforated plate. Furthermore, the present invention provides a producing apparatus for feeding sol having enzymes, plant tissues, etc. dispersed therein onto a perforated plate and dropping the sol into a solidifying liquid in a solidifying liquid tank through orifices in the perforated plate, which comprises a sol supply tank for storing a sol; a sol supply tank moving mechanism for moving up the sol supply tank in proportion to a decrease in the liquid level of the sol supply tank; a planetary gear mechanism having an internal gear formed on the periphery of the perforated plate, a sun gear disposed at the center of the perforated plate, and a planetary gear rotating along the internal gear and the sun gear therebetween; and means for feeding the sol to a position near the outer periphery of said planet gear from said sol supply tank.

In this invention, the sol is fed from the supply tank to a position near the outer periphery of the planet gear of the planetary gear mechanism so that the sol is homogeneously distributed onto the perforated plate. Furthermore, the sol supply tank is raised so that a decrease in the liquid level of the sol supply tank may be compensated so as to keep constant a head between the liquid level of the sol supply tank and the perforated plate. This enables the sol to be fed in a given quantity. Consequently, beads of a uniform diameter are produced, and even fragile substances, such as plant tissues, seeds, etc. can be enclosed in beads without being damaged.

An embodiment of this invention will be explained with reference to the drawings attached hereto.

DETAILED DESCRIPTION OF THE INVENTION

Figure 1:
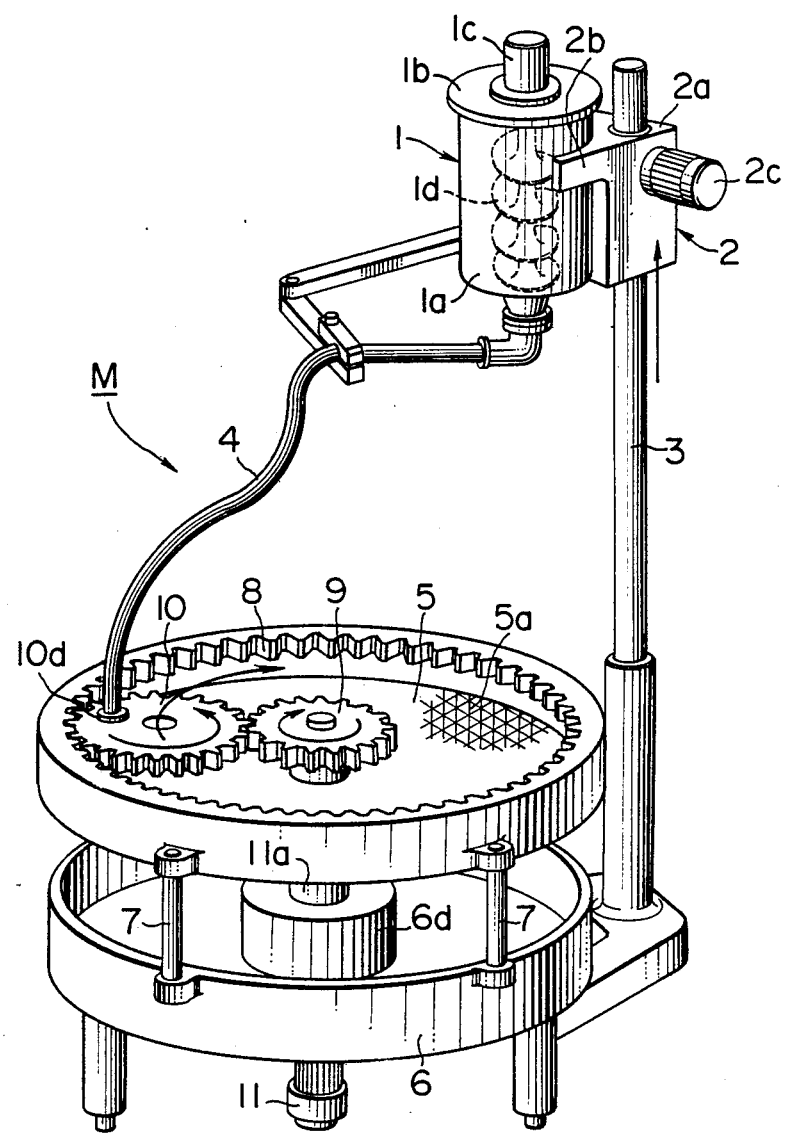
FIG. 1 is a perspective view of the bead producing apparatus according to this invention.
Figure 2:
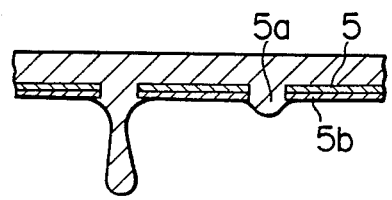
FIGS. 2, 3 and 4 are partial sectional views of the perforated plate used in the bead producing apparatus according to this invention.

Referring to FIG. 1, a bead producing apparatus M of this invention has a sol supply tank 1 for containing sol having enzymes, plant tissues, etc. dispersed therein, and the sol supply tank 1 comprises a cylindrical main body 1a, a lid 1b, a motor 1c mounted on the lid 1b, and a screw 1d turned within the main body 1a by the motor 1c. A sol contained in the main body 1a is, for example, a single solution of sodium alginate, potassium alginate, carboxymethyl cellulose, carrageenan, agar, gelatin, pectin, gellangum or others, or a mixture thereof, and enzymes, plant tissues, etc. dispersed therein. The sol is mixed slowly by the screw 1d in the tank. Enzymes used in this invention are, for example, enzymes, such as glucoamylase, aminoacylase. Organismal material used in this invention includes, for example, lactic acid bacteria, yeast, and other fungi, plant and animal cells, plant tissues, such as somatic embryos, adventitious buds, etc., and seeds. Other enzymes and organismal materials are also suitable for use in this invention.

The sol supply tank 1 is moved up and down by a sol supply tank moving mechanism 2. The mechanism 2 has a moving frame 2a, and the moving frame 2a has arms 2b. The arms 2b are placed around the circumferential surface of the main body 1a to hold the tank 1. A motor 2c is provided on a side surface of the moving frame 2a. The motor 2c drives a rack and pinion mechanism (not shown) to move the moving frame 2a up and down along a pole 3.

The lower end of the sol supply tank 1 is connected to the upper end of a hose 4, so that through the hose a required quantity of the sol in the tank 1 is fed onto a perforated plate 5. The perforated plate 5 has a plurality of orifices $5a$, ... equidistantly formed therein. Underneath the perforated plate 5 there is provided a solidifying liquid tank 6. The perforated plate 5 is supported above the solidifying liquid tank 6 by a plurality of support rods 7.

Complexing agents, solutions, organic solvents, temperature-adjusted fluid paraffin, etc. corresponding to a sol to be used are stored in the solidifying tank 6. For sols and their solidifying solutions, refer to "Suiyousei Koubunshi Mizu Bunsangata Jushi No Saishin Kako Kairyogijitsu to Youto Kaihatu Sogo Gijitsu Shiryoushuu" (Techniques for Most Recent Processing, Quality Improvement and Application Development of Water Soluble Polymers and Water Dispersible Polymers) (1981) published by Keieikaihatsu Center.

The perforated plate 5 has an internal gear 8 formed on its internal periphery. A sun gear 9 is provided at the center of the perforated plate 5. A planet gear 10 is provided between the internal gear 8 and the sun gear 9. A sol supply port $10a$ is formed in the planet gear 10 at a position near the periphery thereof. The lower end of the hose 4 is held in the sol supply port $10a$. The sun gear 9 is fixed to the shaft $11a$ of a motor 11 secured to the underside of the solidifying liquid tank 6 The shaft $11a$ is extended through the bearing portion $6a$ at the center of the solidifying tank and above the perforated plate.

The sun gear 9 rotates thereby causing the planet gear 10 to rotate around the sun gear 9. This planetary gear mechanism enables the sol to be dispersed homogeneously onto the perforated plate 5 from the sol supply port $10a$.

Figure 3:
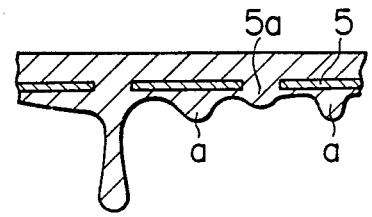

A water-repellent coating of, e.g., TEFLON-brand polytetrafluoroethylene is applied to the underside of the perforated plate 5. Such water-repellency treatment aids the sol which has passed the orifices $5a$ to fall off the underside of the perforated plate 5 in clearcut drops and prevents formation of drops "a" shown in FIG. 3.

Figure 4:
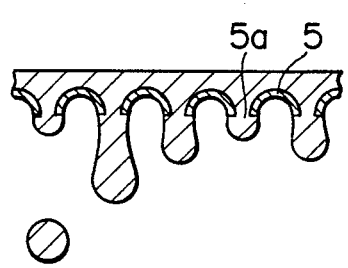

The orifices $5a$ should be configured in the form of a funnel a as shown in FIG. 4, to ensure that uniform ball-shaped beads are produced.

Figure 5:
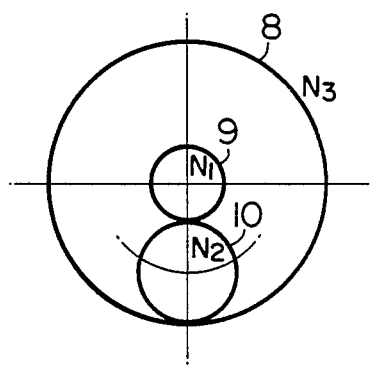
FIG. 5 is a block diagram of the planetary gear mechanism used in the bead producing apparatus according to this invention.

As shown in FIG. 5, when the number of teeth of the internal gear 8 is $N_3$, that of the sun gear 9 is $N_1$, and that of the planet gear 10 is $N_2$, the following equation is derived from the principle of the planetary gear mechanism:

$$N_3 = N_1 + 2N_2.$$

While the planet gear 10 is being revolved one time, the sun gear 9 rotates $1 - N_3/N_1$ times and the planet gear 10 revolves $+N_3/N_2$ times.

It is preferable that a least common multiple (LCM) of $N_1$ and $N_2$ is larger so that the sol supply port $10a$ may not travel always in the same orbit. To give examples, (1) $N_1 = 30$, $N_2 = 50$, LCM = 150
(2) $N_1 = 31$, $N_2 = 51$, LCM = 1581
(3) $N_1 = 29$, $N_2 = 53$, LCM = 1537

Figure 7:
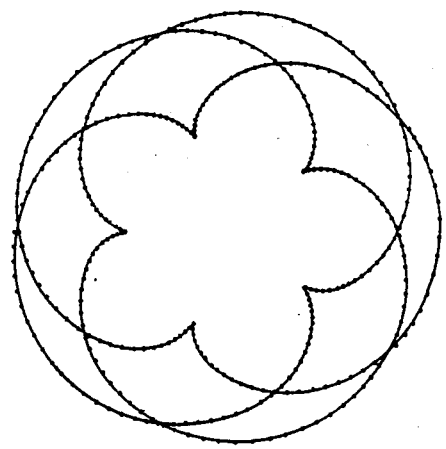
FIGS. 7 to 11 are views of orbits in which the sol supply port of the bead producing apparatus of this invention travels.
Figure 8:
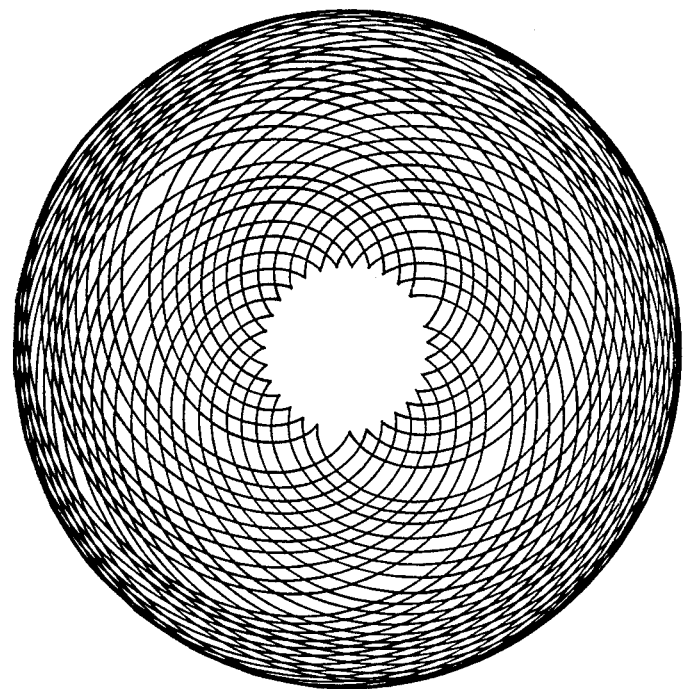
Figure 9:
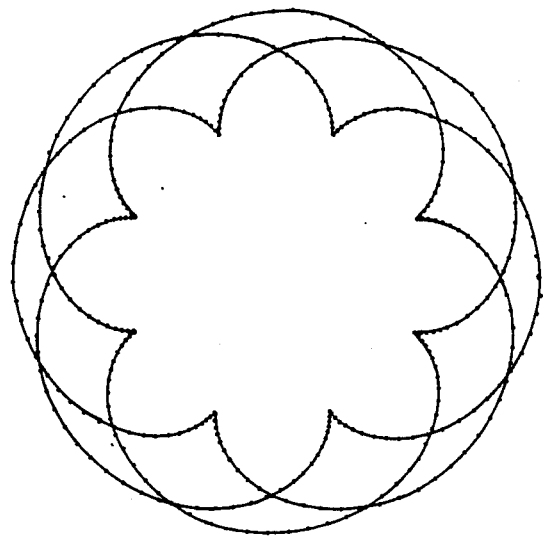
Figure 10:
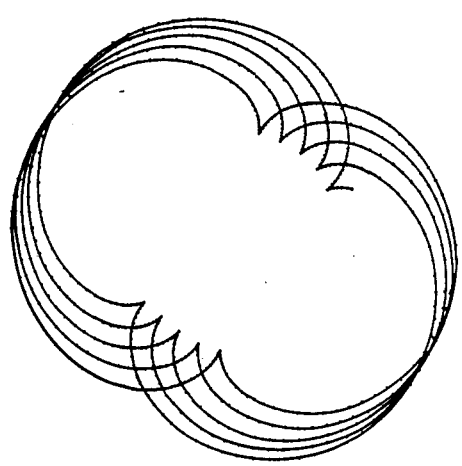
Figure 11:
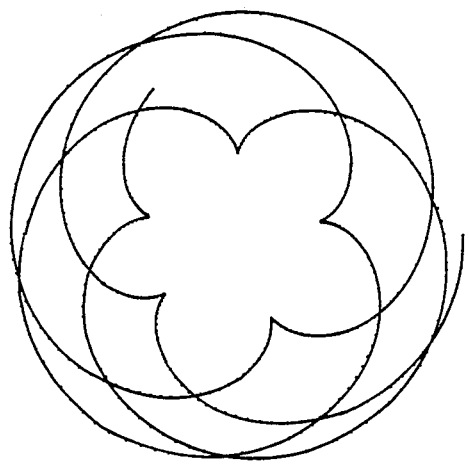

In Example (1) described above, the orbit of FIG. 7 (at the beginning of a cycle) is depicted. In Example (2) described above, the orbit of FIG. 8 almost at the end of a cycle is depicted. In addition, when $N_1 = 80$ and $N_2 = 30$, the orbit at the start of a cycle is as shown in FIG. 9. When $N_1 = 60$ and $N_2 = 31$, the orbit of FIG. 10 is obtained. When $N_1 = 47$ and $N_2 = 37$, the orbit of FIG. 11 is obtained. Of these various orbits, the orbit of FIG. 8 for a larger LCM described above, and that of FIG. 11 are preferable. The orbit of FIG. 10 is deflected, and the orbit of FIG. 9 is well-balanced but has a large vacant area at the center.

Figure 6:
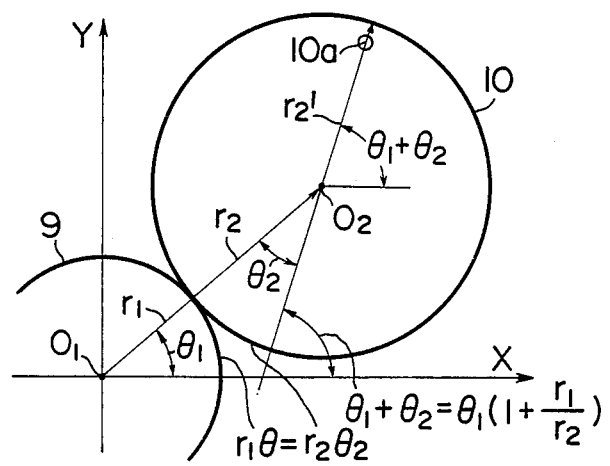
FIG. 6 is coordinate explaining orbits in which the sol supply port of the bead producing apparatus of this invention moves.

These orbits are depicted as shown in FIG. 6. When an x-axis and a y-axis are set with the center of the sun gear 9 as an origin $O_1$, and with the center of the planet gear 10 as an origin $O_2$, and the sun gear 9 rotates by $\theta_1$, the planet gear 10 rotates by $\theta_2$ in the opposite direction to that of the sun gear 9. The coordinates of the sol supply port $10a$ at this time are $$X = (r_1 + r_2) \cos \theta_1 + r_2' \cos(\theta_1 + \theta_2) \quad (1)$$
$$Y = (r_1 + r_2) \sin \theta_1 + r_2' \sin(\theta_1 + \theta_2), \quad (2)$$

wherein $r_2'$ 2 is a distance from the center $O_2$ of the planet gear 10 to the sol supply port $10a$. $r_1$ and $r_2$ are radii of the sun gear and the planet gear respectively. Accordingly $r_1\theta_1 = r_2\theta_2$ is given. Therefore, 225

$$\theta_1 + \theta_2 = \theta_1(1 + r_1/r_2).$$

Assuming $r_2 = r_2'$ and substituting the above-described equations respectively with $\theta_1 + \theta_2 = \theta_1(1 + r_1/r_2)$, $$X = (r_1 + r_2) \cos \theta_1 + r_2 \cos \theta_1(1 + r_1/r_2) \text{ and} \quad (1)$$
$$Y = (r_1 + r_2) \sin \theta_1 + r_2 \sin \theta_1(1 + r_1/r_2). \quad (2)$$

FIGS. 7 to 11 show that the orbits of the sol supply port as depicted in computer simulations based on the above-described equations.

For example, to form 4mm-diameter beads, a sol flows through a 10mm-diameter hose 4 at a flow rate of 10cm/sec to be fed on the perforated plate 5. In one hour, $\pi \times \{1(cm)/2\}^2 \times 10 \times 3600 \ (sec) = 4/3 + \pi \times (0.4/2)^3 \times N$ (number of beads), and therefore, $N = 843750$ pieces/hour $= 234$ pieces/sec are obtained. This shows a sufficient number of beads can be formed in a given hour by feeding sol even through the hose 4.

In order to feed a constant quantity of sol to the sol supply port $10a$, the liquid level of the sol supply tank is made constant with respect to the perforated plate 5 (that is, a head is made constant). To accomplish this purpose, the moving frame $2a$ is moved up at a given rate in proportion to a decrease in the liquid level The embodiment of the present invention having the above-described structure enables a given quantity of sol to be distributed evenly on the perforated plate and consequently to be formed into beads of a uniform diameter In addition, the present embodiment enables fragile substances, such as plant tissues, seeds, etc. to be enclosed in beads without being damaged.

What is claimed is:

1. A method for producing beads from sol comprising:
    feeding said sol from a sol supply tank to a position near the outer periphery of a planet gear of a planetary gear mechanism disposed on a perforated plate as said planet gear rotates; and
    dropping sol as droplets through an orifice in said perforated plate into a tank containing liquid that solidifies droplets into beads.

2. The method of claim 1 further comprising the step of:
    moving the sol supply tank vertically upwards to compensate for decrease in sol volume so that the sol head pressure remains approximately constant and beads of uniform size are produced.

3. A bead producing apparatus for feeding sol onto a perforated plate and dropping said sol into solidifying liquid in a solidifying liquid tank through orifices provided in said perforated plate, comprising:

a sol supply tank for storing said sol;

a perforated plate;

an internal gear formed on the internal periphery of said perforated plate;

a sun gear disposed at the center of said perforated plate;

a planetary gear mechanism having a planet gear rotating around said sun gear and along said internal gear therebetween;

means for feeding said sol to a position near the outer periphery of said planet gear from said sol supply tank; and a tank for containing liquid which solidifies said beads.

4. The apparatus of claim 3 further comprising means for moving the sol supply tank in proportion to a decrease in the liquid level of the sol supply tank.

5. A bead producing apparatus according to claim 3 wherein said plate has a water-repellent coating on the underside.

6. A bead producing apparatus according to claim 5 wherein said water-repellent coating comprises polytetrafluoroethylene.

7. A bead producing apparatus according to claim 6 wherein said polytetrafluoroethylene coating comprises TEFLON.

8. A bead producing apparatus according to claim 3 wherein said orifices formed in said perforated plate have cross-sections which approximate an inverted frustocone.

* * * * *

UNITED STATES PATENT AND TRADEMARK OFFICE
CERTIFICATE OF CORRECTION

PATENT NO. : 4,933,122
DATED : June 12, 1990
INVENTOR(S) : SUZUKI ET AL.

It is certified that error appears in the above - identified patent and that said Letters Patent is hereby corrected as shown below:

Column 3, line 24, please insert --.-- after "6";

Column 3, line 40, please insert --,-- after "funnel";

Column 3, line 51, please delete "+$N_3/N_2$" and insert therefor --1+$N_3/N_2$--;

Column 4, line 13, please delete "2" before "is";

Column 4, line 17, please delete "225";

Column 4, line 34, please delete "+" after "4/3" and substitute therefor --X--; and Column 4, lines 49-50, please insert --.-- after "diameter".
Column 3, line 40, delete the "a" after funnel.

Signed and Sealed this

Seventeenth Day of December, 1991

*Attest:*

HARRY F. MANBECK, JR.

*Attesting Officer*          *Commissioner of Patents and Trademarks*